(12) United States Patent
Siess et al.

(10) Patent No.: US 7,736,296 B2
(45) Date of Patent: Jun. 15, 2010

(54) INTRACARDIAC BLOOD PUMP

(75) Inventors: Thorsten Siess, Wuerselen (DE); Frank Kirchhoff, Uebach-Palenberg (DE)

(73) Assignee: Abiomed Europe GmbH, Aachen (DE)

( * ) Notice: Subject to any disclaimer, the term of this patent is extended or adjusted under 35 U.S.C. 154(b) by 466 days.

(21) Appl. No.: 11/664,433

(22) PCT Filed: Sep. 23, 2005

(86) PCT No.: PCT/EP2005/054767

§ 371 (c)(1),
(2), (4) Date: Mar. 30, 2007

(87) PCT Pub. No.: WO2006/040252

PCT Pub. Date: Apr. 20, 2006

(65) Prior Publication Data

US 2008/0086027 A1  Apr. 10, 2008

(30) Foreign Application Priority Data

Oct. 14, 2004  (DE)  ........................ 10 2004 049 986

(51) Int. Cl.
*A61M 1/12* (2006.01)

(52) U.S. Cl. .............................. 600/16; 600/17; 600/18; 623/3.1; 623/3.13; 604/65; 604/121; 604/151; 128/898

(58) Field of Classification Search .................. 600/15, 600/16, 17, 18; 623/3.1, 3.13–3.15; 417/394, 417/390; 604/6.01–6.04
See application file for complete search history.

(56) References Cited

U.S. PATENT DOCUMENTS

| 5,964,694 A | * | 10/1999 | Siess et al. ..................... 600/17 |
| 6,058,593 A | * | 5/2000 | Siess ........................... 29/596 |
| 2003/0187322 A1 | | 10/2003 | Siess |

* cited by examiner

*Primary Examiner*—Carl H Layno
*Assistant Examiner*—Paula J Stice
(74) *Attorney, Agent, or Firm*—Fulwider Patton LLP

(57) ABSTRACT

Disclosed is an intracardiac blood pump with a flexible screen between which discharge ports are located. The pump parts are connected to the flexible screen which catches the axially discharged flow and deflects the same in an axial direction. The delivery rate of the pump is increased by preventing impact losses and swirls at the discharge ports.

6 Claims, 4 Drawing Sheets

INTRACARDIAC BLOOD PUMP

The invention relates to an intracardiac blood pump with a drive portion including a motor and a pump portion including a pump wheel driven by the motor, at least one lateral discharge port being provided between the drive portion and the pump portion, and further with a screen attached to the pump portion and covering the discharge ports.

An intracardiac blood pump is a blood pump that is at least partially introduced into the heart to deliver blood from the heart into an artery, wherein the pump may protrude through a surgical opening in the heart. Such intracardiac blood pumps have a maximum outer diameter of about 10-15 mm. A special form of intracardiac blood pumps are intravascular blood pumps. They are introduced into the heart through the vascular system of the patient, the incision site being spaced from the heart. Intravascular blood pumps have a diameter of about 8 mm at maximum and a rigid length of 35 mm at maximum. The delivery rate is approx. 4.5 l/min at physiological pressures of 60 to 80 mmHg.

DE 100 40 403 (Impella) describes an intracardiac blood pump on which the precharacterizing part of claim 1 is based. The discharge ports are covered by a tubular screen. The screen causes an effective shortening of the structural length of the blood pump in the case that the blood pump is placed in a heart valve and delivers into an artery. This requires the screen to form an elongate tube that covers a substantial part of the pump portion and the drive portion.

Another intracardiac blood pump, described in DE 103 36 902 B3 (Impella), comprises a pump having its distal end connected to a flexible cannula. At the distal end of the cannula, a suction head is provided for taking in the blood. The suction head is extended by a non-sucking extension. The same stabilizes the position of the pump device in the heart.

With an intracardiac blood pump, obtaining a high output is of importance. The output can be increased by increasing the pumping rotation speed, however, the risk of damage to the blood sets limits to this possibility.

It is an object of the invention to provide an intracardiac blood pump delivering an increased output.

The blood pump of the present invention is defined in claim 1. According to the invention, it is provided that the screen projects from the pump portion at the upstream end of the discharge ports, such that the flow leaving the discharge ports is passed smoothly to an oblique guide portion of the screen.

The invention provides for an impact-free smooth transition from the inside of the pump into the axially directed outer flow. It is based on the insight that, in prior art, impact losses and turbulences occur when the blood passes through the discharge ports, causing a great part of the kinetic energy to be lost by dissipation. According to the invention, these losses are avoided by the flow-guiding effect of the screen. Thus, it is not the purpose of the screen to keep the discharge ports clear, but it causes the passage of the flow passing the discharge ports to an oblique guide portion of the screen. This oblique guide portion is immediately contiguous to the discharge openings so that neither turbulent zones nor dead water zones are formed. Tests have shown that through this design of the screen, the delivery rate of the pump can be augmented by 10 to 20% under otherwise similar conditions (same differential pressure and same rotational speed).

In a preferred embodiment of the invention, the screen is flexible. This means that the screen may deformed to be folded and laid on the outer wall of the pump. Without the action of external force, the screen automatically assumes its operating position. For example, the screen is a thin skin of polyurethane with a thickness of 0.1 to 0.2 mm. On the other hand, the screen must have such a rigidity that it stays open also during the hydraulic pressure decrease caused by the flow.

Preferably, the pump wheel has blades extending to below the discharge ports. Thus, the structural length of the pump can be reduced, while the hydraulic power can be increased at the same time. The parts of the blades located below the discharge ports deliver radially immediately against the oblique screen. The screen also prevents body tissue from entering into the vicinity of the blades and being damaged by them. Thus, the screen contributes to an increase in the product safety of the intracardiac blood pump.

The screen may be turned by more than 90 degrees against the flow direction and may be placed against the pump portion. This is necessary, if the blood pump has been introduced into the body through a tubular introducer sheath and has to be withdrawn through the same lock. Whereas the flexible screen can be placed against the outer wall of the pump when pushed, the screen in the unfolded condition would prevent the withdrawal of the pump through the introducer sheath. As a consequence of the possibility to turn or fold the screen, the screen in the turned condition is pressed against the pump portion so that the pump can be withdrawn through the tubular introducer sheath in this condition.

The guide portion of the screen may be conical or concavely curved, e.g. form an exponential extension. In any case, the screen constantly widens over its entire length.

A particular embodiment of the invention provides that holding members engage the flared end of the screen, which are attached to the drive portion and radially retract the screen when the blood pump is pulled into an introducer sheath.

The screen may be an integral part of a cannula fastened to the pump portion. On the other hand, the screen may also be fastened to the pump portion by gluing or any suitable means.

The following is a detailed description of embodiments of the invention with reference to the drawings.

IN THE FIGURES

Figure 1:
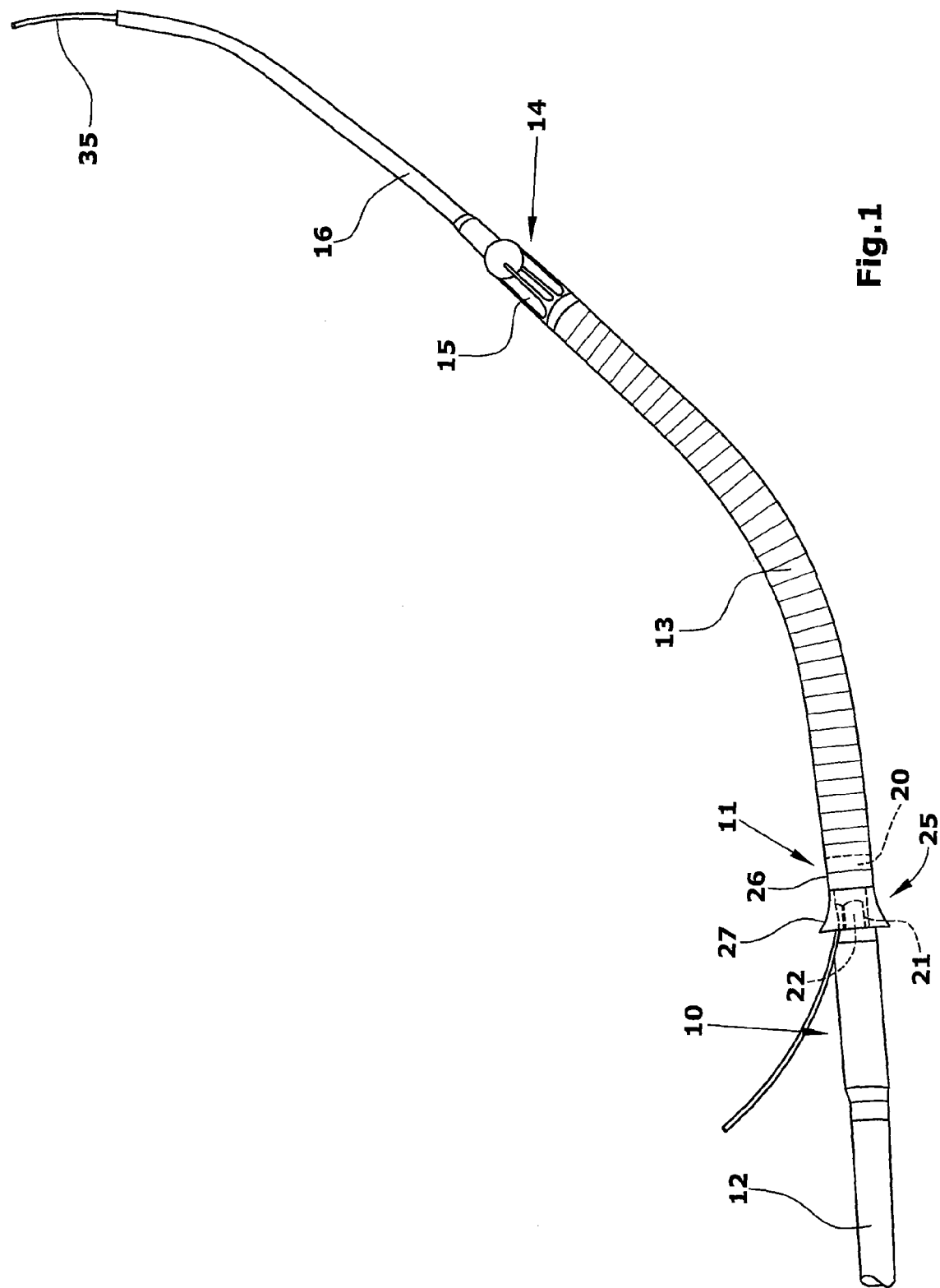
FIG. 1 is an illustration of the intracardiac blood pump with a guide wire attached for positioning.

The intracardiac pump device comprises a drive portion 10 and a pump portion 11 coaxial thereto. The drive portion 10 includes a motor (not illustrated). The proximal end of the drive portion 10 is connected with a catheter 12 holding the electric lines for operating and controlling the blood pump. The pump portion 11 is connected with a cannula 13 in the form of an elongate flexible hose whose distal end is provided with a suction head 14 having inflow openings 15. Contiguous to the suction head 14 is a soft elastic extension 16 that mechanically, yet not hydraulically extends the cannula 13. This extension 16 is provided with a pigtail tip to allow for atraumatic support on body tissue.

The general structure of the blood pump corresponds to the pump device described in DE 103 36 902 B3.

The pump portion 11 has a pump ring 20 that is connected with the drive portion 10 through longitudinally extending webs 21. Between the webs 21, the discharge ports 22 are situated through which blood exits radially to then flow along the outer side of the drive portion 10.

According to the invention, the screen 25 is provided at the pump portion 11. It comprises an annular sleeve 26 sitting on the pump ring 20 and a continuously flaring guide portion 27 projecting proximally from the pump ring. The beginning of the guide portion 27 is at the upstream end of the discharge ports 22, i.e. at the end adjoining the pump ring 20.

In the embodiment of FIG. 1, the screen 25 is of a concave shape. It has an exponential contour with the guide portion 27 progressively widening. The screen 25 is annular and closed circumferentially.

Figure 2:
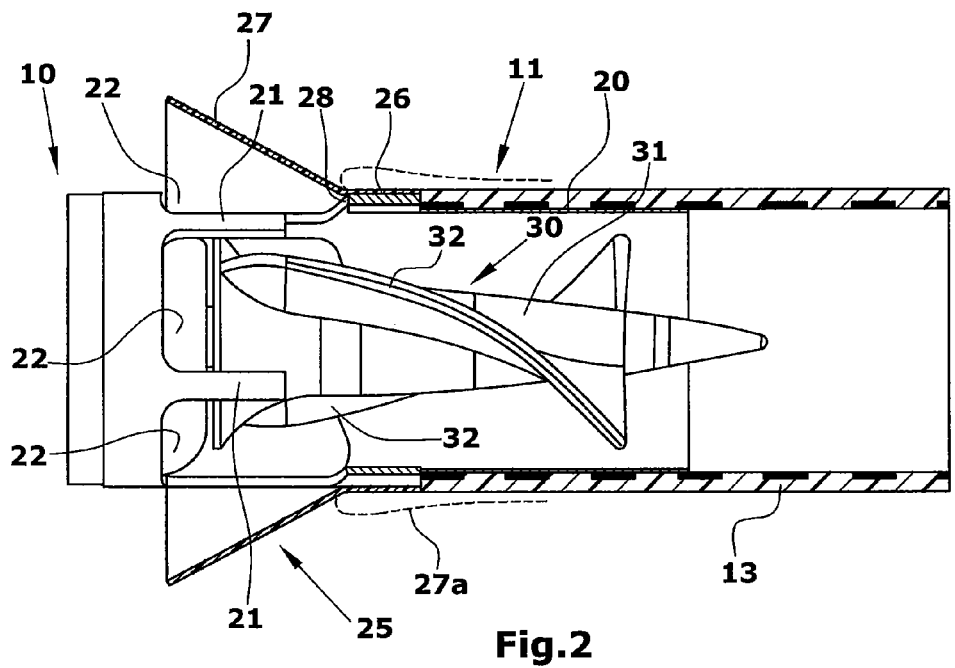
FIG. 2 is a longitudinal section through the pump portion.

FIG. 2 is an enlarged longitudinal section through the pump portion. The pump wheel 30 extends longitudinally through the pump ring 20. It has a hub 31 with radially projecting helical blades 32. The diameter of the hub 31 becomes larger in the flow direction. The blades 32 extend to the vicinity of the discharge ports 22. More than half the length of the discharge ports 22 covers the blades 32.

The guide portion 27 immediately adjoins the upstream end 28 of the discharge ports 22. In FIG. 2, the guide portion 27 is conical.

The flow delivered in an axial direction by the pump wheel 30 is deflected radially outward by the hub 31 and is smoothly redirected into the axial direction by the oblique guide portion 27 of the screen 25. The length of the screen 25 is such that the screen just covers the discharge ports 22.

In a practical embodiment of an intracardiac blood pump, the outer diameter of the drive portion 10 and of the pump portion 11 is 4.0 mm. The outer diameter of the screen 25 is 5.6 to 6.0 mm. The wall thickness of the screen is 0.1 to 0.2 mm. The screen is made of a flexible material, for example of polyurethane. It may be formed integral with the cannula 13.

Figure 3:
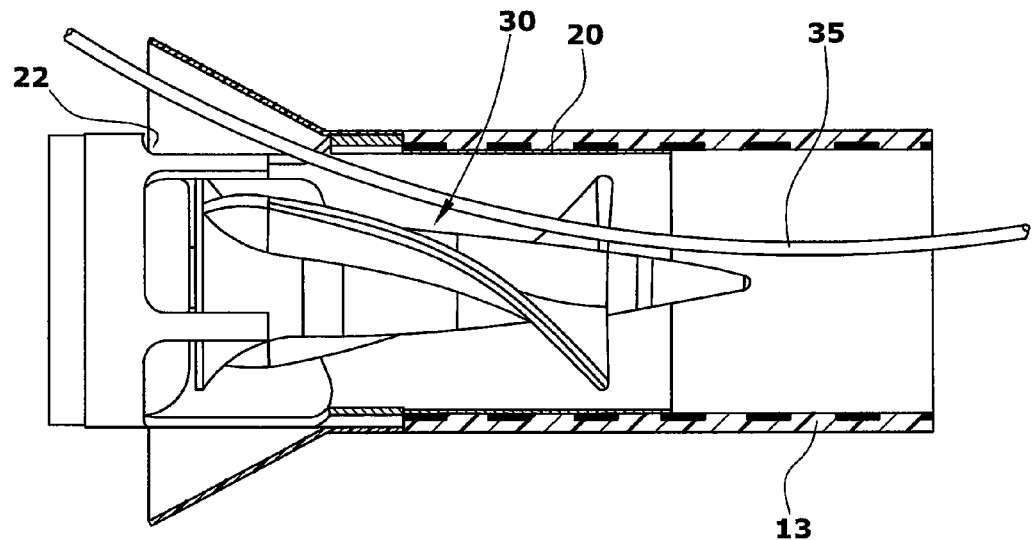
FIG. 3 shows the pump portion of FIG. 2 with a guide wire inserted therethrough.

FIG. 3 illustrates the same part of the pump as FIG. 2, however, with a guide wire 35 introduced additionally. The guide wire that serves to position the blood pump is first advanced into the body of a patient. The blood pump, together with the catheter, is then slipped over the same. The guide wire is guided laterally past the drive portion 10 and enters one of the discharge ports 22 to then extend through the cannula 13 and the extension 16. After the catheter and the blood pump have been placed, the guide wire is withdrawn.

The intravascular blood pump is inserted into the patient's body through a tubular introducer sheath. Here, the outer diameter of the blood pump is slightly smaller than the inner diameter of the introducer sheath. During insertion, the flexible screen 25 comes to lie against the outer surface of the blood pump, whereby the discharge ports 22 are closed. When the blood pump has exited the distal end of the introducer sheath, the screen 25 unfolds automatically. It is a problem to remove the blood pump from the patient's body. Upon withdrawal, the screen 25 would get caught at the distal end of the introducer sheath and prevent the blood pump from being withdrawn through the introducer sheath. Due to the flexibility of the screen 25, the guide portion of the screen turns over so that the screen is folded about the sleeve 26 by more than 90 degrees and then rests against the cannula 13. In this condition, the blood pump can be withdrawn through the introducer sheath. In FIG. 2, the guide portion 27a folded over is shown in dashed lines.

Figure 4:
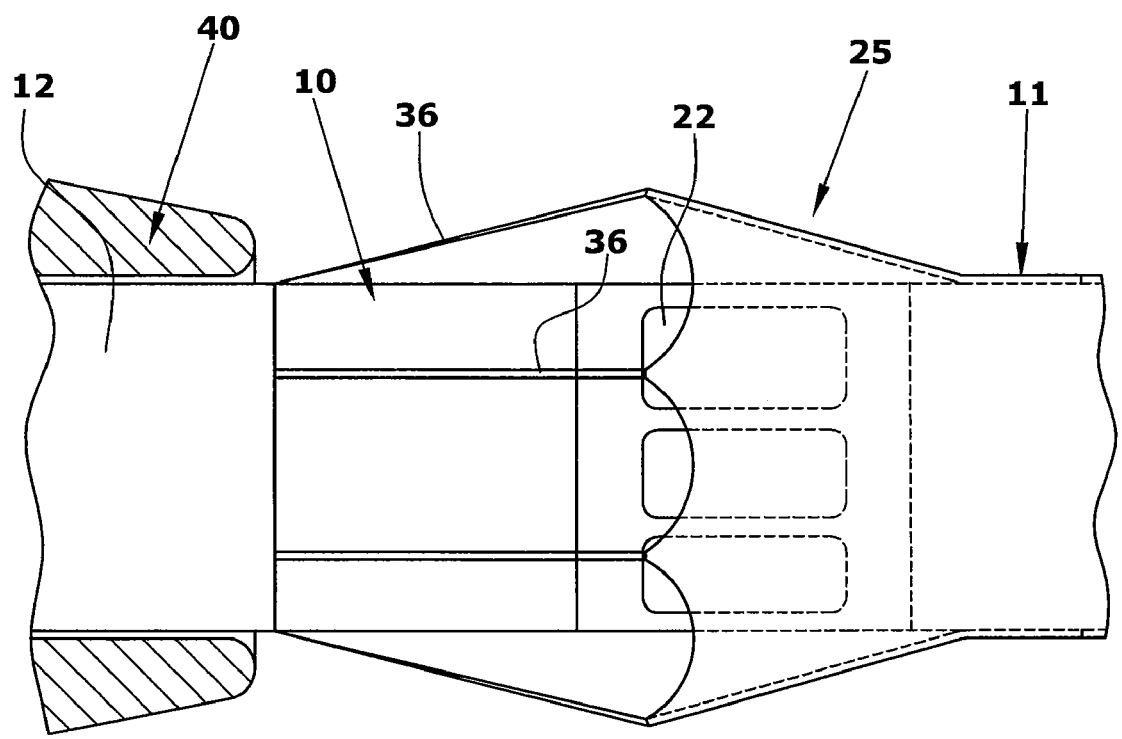
FIG. 4 shows an embodiment, wherein the screen is collapsed as it is withdrawn into an introducer sheath.

FIG. 4 illustrates another embodiment. Here, the outer end of the screen 25 is connected with rod-shaped holding members 36 that are fastened to the drive portion 10. In FIG. 4, the distal end of an introducer sheath 40 is illustrated through which the blood pump is advanced. Upon withdrawal, the holding members 36 abut against the end of the introducer sheath 40 and come to lie on the outer surface of the blood pump, taking the screen 25 along in the manner of a sail.

A typical inner diameter of the introducer sheath 40 for a catheter of 12F (corresponding to an outer diameter of 4 mm) is 3.33 mm (13F).

Figure 5:
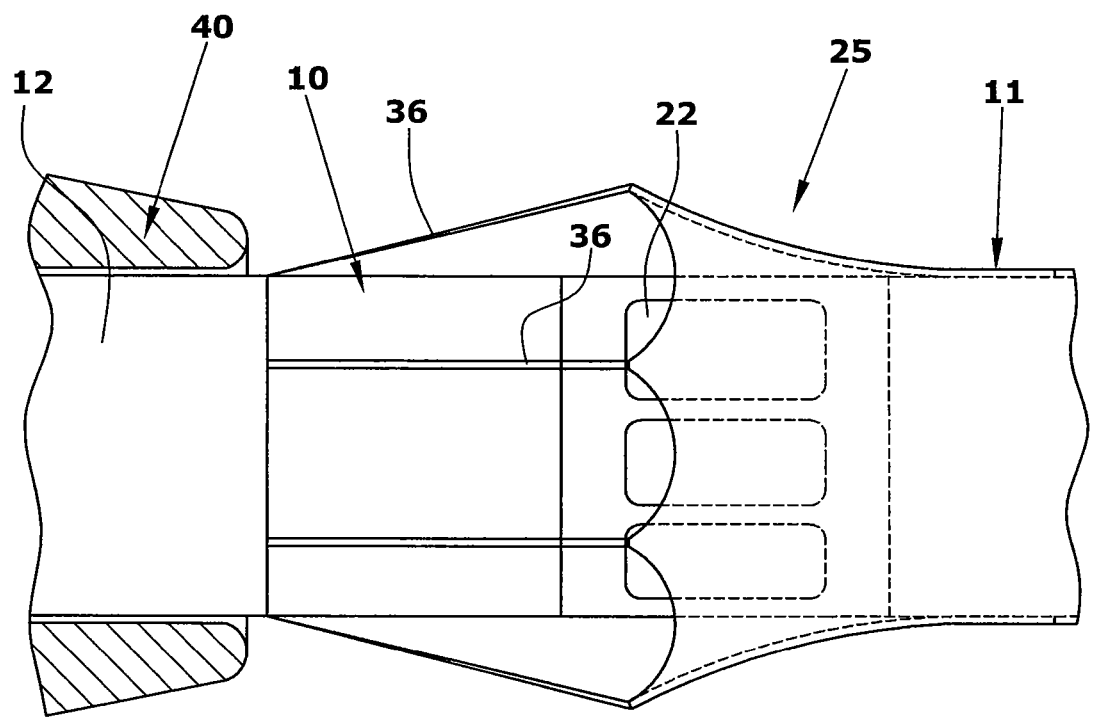
FIG. 5 shows an alternative embodiment of the embodiment shown in FIG. 4.

FIG. 5 shows a further embodiment wherein the guide portion 27a of the screen has a shape with an exponential cross-section.

We claim:

1. An intracardiac blood pump comprising a proximal drive portion including a motor, a distal pump portion including a pump wheel driven by the motor, lateral discharge ports being provided between the drive portion and the pump portion, and further comprising a screen attached to the pump portion and covering the discharge ports, characterized in that
   the screen has a closed sidewall with a distal end attached about the pump portion and an open proximal end and wherein the screen projects from the pump portion at a distal upstream end of the discharge ports, such that flow leaving the discharge ports is guided smoothly by an oblique guide portion of the screen and further characterized in that the screen is flexible and adapted to be turned over by more than 90 degrees against the flow direction and to be placed against the pump portion.

2. An intracardiac blood pump comprising a proximal drive portion including a motor, a distal pump portion including a pump wheel driven by the motor, lateral discharge ports being provided between the drive portion and the pump portion, and further comprising a screen attached to the pump portion and covering the discharge ports, characterized in that
   the screen has a closed sidewall with a distal end attached about the pump portion and an open proximal end and wherein the screen projects from the pump portion at a distal upstream end of the discharge ports, such that flow leaving the discharge ports is guided smoothly by an oblique guide portion of the screen and further characterized in that the guide portion of the screen is conical.

3. An intracardiac blood pump comprising a proximal drive portion including a motor, a distal pump portion including a pump wheel driven by the motor, lateral discharge ports being provided between the drive portion and the pump portion, and further comprising a screen attached to the pump portion and covering the discharge ports, characterized in that
   the screen has a closed sidewall with a distal end attached about the pump portion and an open proximal end and wherein the screen projects from the pump portion at a distal upstream end of the discharge ports, such that flow leaving the discharge ports is guided smoothly by an oblique guide portion of the screen and further characterized in that the guide portion of the screen has a shape with an exponential cross-section.

4. An intracardiac blood pump comprising a proximal drive portion including a motor, a distal pump portion including a pump wheel driven by the motor, lateral discharge ports being provided between the drive portion and the pump portion, and further comprising a screen attached to the pump portion and covering the discharge ports, characterized in that
   the screen has a closed sidewall with a distal end attached about the pump portion and an open proximal end and wherein the screen projects from the pump portion at a distal upstream end of the discharge ports, such that flow leaving the discharge ports is guided smoothly by an oblique guide portion of the screen and further characterized in that the screen is constantly flared over its entire length.

5. An intracardiac blood pump comprising a proximal drive portion including a motor, a distal pump portion including a pump wheel driven by the motor, lateral discharge ports being provided between the drive portion and the pump portion, and further comprising a screen attached to the pump portion and covering the discharge ports, characterized in that
    the screen has a closed sidewall with a distal end attached about the pump portion and an open proximal end and wherein the screen projects from the pump portion at a distal upstream end of the discharge ports, such that flow leaving the discharge ports is guided smoothly by an oblique guide portion of the screen and further characterized in that holding members engage the flared end of the screen, which are fastened at the drive portion and radially retract the screen when the blood pump is pulled into an introducer sheath.

6. An intracardiac blood pump comprising a proximal drive portion including a motor, a distal pump portion including a pump wheel driven by the motor, lateral discharge ports being provided between the drive portion and the pump portion, and further comprising a screen attached to the pump portion and covering the discharge ports, characterized in that
    the screen has a closed sidewall with a distal end attached about the pump portion and an open proximal end and wherein the screen projects from the pump portion at a distal upstream end of the discharge ports, such that flow leaving the discharge ports is guided smoothly by an oblique guide portion of the screen and further characterized in that a canula is fastened to the pump portion and the screen is an integral part of the canula.

\* \* \* \* \*